(12) United States Patent
Li et al.

(10) Patent No.: US 7,125,713 B2
(45) Date of Patent: Oct. 24, 2006

(54) HUMAN MULLERIAN DUCT-DERIVED EPITHELIAL CELLS AND METHODS OF ISOLATION AND USES THEREOF

(75) Inventors: Rong-hao Li, La Jolla, CA (US); Jennie Powell Mather, Millbrae, CA (US)

(73) Assignee: Raven biotechnologies, inc., South San Francisco, CA (US)

( * ) Notice: Subject to any disclaimer, the term of this patent is extended or adjusted under 35 U.S.C. 154(b) by 428 days.

(21) Appl. No.: 10/117,895

(22) Filed: Apr. 5, 2002

(65) Prior Publication Data

US 2003/0040110 A1  Feb. 27, 2003

Related U.S. Application Data

(62) Division of application No. 09/545,435, filed on Apr. 7, 2000, now Pat. No. 6,416,999.

(51) Int. Cl.
  A01N 1/00 (2006.01)
  C12P 21/04 (2006.01)
  C12N 15/63 (2006.01)
  C07K 16/00 (2006.01)

(52) U.S. Cl. .................. 435/325; 435/1.1; 435/70.1; 435/21.1; 435/455; 530/387.1

(58) Field of Classification Search ............... 435/325, 435/1.1, 70.1, 71.1, 69.3, 455; 530/387.1
  See application file for complete search history.

(56) References Cited

U.S. PATENT DOCUMENTS

| | | | |
|---|---|---|---|
| 6,004,528 A | 12/1999 | Bergstein | |
| 6,194,203 B1 | 2/2001 | Blum et al. | |
| 6,416,999 B1 | 7/2002 | Li et al. | |

FOREIGN PATENT DOCUMENTS

| | | |
|---|---|---|
| EP | 0 802 257 A1 | 10/1997 |
| WO | WO-01/077298 A2 | 10/2001 |
| WO | WO-01/077298 A3 | 10/2001 |

OTHER PUBLICATIONS

Barnes and Sato, (1980). "Methods for growth of cultured cells in serum-free medium" *Anal. Biochem.* 102:255-270.
Buck et al., (1982). "Monoclonal antibodies specific for cell culture mycoplasmas" *In Vitro* 18(4):377-381.
Freshney, R.I. (ed), (1987). *Animal Cell Culture* pp. vii-xii. (Table of Contents).
Ganong, William F., (1991). "The gonads: Development & function of the reproductive system" in *Review of Medical Physiology*, fifteenth edition, Appleton and Lange, (eds), Chapter 23, pp. 387-425.
Ham and McKeehan, (1979). "Media and growth requirements" *Meth. Enzy.* 58:44-93.
Harlow and Lane (eds), (1988). *Antibodies, A Laboratory Manual* pp. iii-ix. (Table of Contents).
Jacob et al., (1999). "Early development of the Müllerian duct in avian embryos with reference to the human" *Cells Tissues Organs* 164:63-81.
Jacobi, P. et al. (1997). "Expression of the CD15 Differentiation Antigen in the Reproductive Tract of the Female Rat During Fetal and Early Postnatal Ontogeny," *Histochem. Cell Biol.* 108:57-66.
Köhler et al., (1975). "Continuous cultures of fused cells secreting antibody of predefined specificity" *Nature* 256:495-497.
Lawrence et al., (1992), "An ultrastructural study of the developing urogenital tract in early human fetuses" *Amer. J. Obstetrics/Gynecol.* 167:185-193.
Mather, Jennie P. and Roberts, Penelope E., (1998). *Introduction to Cell and Tissue Culture* Plenum Press, New York pp. xi-xv. (Table of Contents).
Paranko, J. and Virtanen, I. (1986). "Epithelial and Mesenchymal Cell Differentiation in the Fetal Rat Genital Ducts: Changes in the Expression of Cytokeratin and Vimentin Type of Intermediate Filaments and Desmosomal Plaque Proteins," *Develop. Biol* 117:135-145.
Pellegrini et al., (1997). "*Emx2* developmental expression in the primordia of the reproductive and excretory systems" *Anat. Embryol.* 196:427-433.
Pisani et al., (1993). "Estimates of the worldwide mortality from eighteen major cancers in 1985. Implications for prevention and projections of future burden" *Int. J. Cancer* 55:891-903.
Stephan, Jean-Philippe et al., (Dec. 1997). "Characterization of Cell Surface Proteins Using Antibodies Raised to Antigens From Pancreatic Cell Lines," Abstract 1905-presentation materials:17 pages.
Taylor et al., (1997). "A conserved *Hox* axis in the mouse and human female reproductive system: Late establishment and persistent adult expression of the *Hoxa* cluster genes" *Biol. Reprod.* 57:1338-1345.
Viehban, C. et al. (1987). "The Mesonephric (Wolffian) and Paramesonephric Müllerian Ducts of Golden Hamsters Express Different Intermediate-Filament Proteins During Development," *Differentiation* 34:175-188.
MacLaughlin, D.T. et al. (1992). "Mullerian Duct Regression and Antiproliferative Bioactive of Mullerian Inhibiting Substance Reside inits Carboxy-Terminal Domain," *Endocrinology* 131:291-296.

(Continued)

*Primary Examiner*—Joseph Woitach
(74) *Attorney, Agent, or Firm*—Morrison & Foerster LLP

(57) ABSTRACT

This invention discloses a substantially pure population of human Müllerian duct-derived epithelial cells and methods of isolating and culturing the Müllerian duct-derived epithelial cells. By carefully manipulating the microenvironment in which the Müllerian duct-derived epithelial cells are grown, multiple passages are attainable wherein the Müllerian duct-derived epithelial cells are capable of becoming uterine, cervical, vaginal, and oviductal cells. In addition, several uses of human Müllerian duct-derived epithelial cells and cells differentiating therefrom are disclosed herein.

4 Claims, 4 Drawing Sheets
(1 of 4 Drawing Sheet(s) Filed in Color)

OTHER PUBLICATIONS

Tsuji, M. et al. (1992). "Effect of Human Recombinant Mullerian Inhibiting Substance on Isolated Epithelial and Mesenchymal Cells During Mullerian Duct Regression in the Rat," 131(3):1481-1488.

Kelch, R.P. et al. (1971). "Testoterone Metabolism in Target Tissues: 2. Human Fetal and Adult Reproductive Tissues, Perineal Skin and Skeletal Muscle," 32:449-456.

Josso, N. et al., (1971) "Interspecific character of the mullerian-inhibiting substance: action of the human fetal testis, ovary and adrenal on the fetal rat mullerian duct in organ culture" *J. Clin. Endocr.* 32:404-409.

Magro, G. et al. (1995) "Expression of cytokeratins, vimentin and basement membrane components in human fetal male mullerian duct and perimullerian mesenchyme" *Acta Histochemic* (97):13-18.

Loo, D.T. et al. (Apr. 10, 1987). "Extended Culture of Mouse Embryo Cells Without Senescence: Inhibition by Serum," *Science* 236(4798):200-202.

Mather, J.P. et al. (1979). "The Use of Hormone-Supplemented Serum-Free Media in Primary Cultures," *Experimental Cell Research* 124:215-221.

HUMAN MULLERIAN DUCT-DERIVED EPITHELIAL CELLS AND METHODS OF ISOLATION AND USES THEREOF

CROSS-REFERENCE TO RELATED PATENT APPLICATION

This application is a divisional of U.S. patent application Ser. No. 09/545,435, filed on Apr. 7, 2000 now U.S. Pat. No. 6,416,999, the entirety of which is hereby incorporated by reference.

TECHNICAL FIELD

This invention is in the field of developmental biology and cell biology. Specifically, this invention relates to a population of Müllerian duct-derived epithelial cells that are capable of differentiating into uterine, oviductal, vaginal, and cervical cells, methods of isolating the Müllerian duct-derived epithelial cells, characterization of Müllerian duct-derived epithelial cells, and uses of the Müllerian duct-derived epithelial cells.

BACKGROUND ART

In the past few decades, a substantial amount of time and effort has been put into researching the development of female reproductive organs. The impetus behind the research varies from laboratory to laboratory, however, all the research efforts address important common issues relating to the overall health of women. Some of these issues include: cervical cancer, infertility, endometriosis, uterine cancer, ectopic pregnancies, ovarian cysts, and uterine fibroids. Cervical cancer, for example, is a particularly important topic for women's health considering that cervical cancer is the second most common cancer among women worldwide with approximately 450,000 new cases being diagnosed annually and that almost 200,000 deaths are due to cervical cancer. Pisani et al. *Int. J. Cancer* 55: 891–903 (1993). Although the etiological cause of cervical cancer remains unknown today, there are many reports that infection with human papillomavirus, in particular, HPV-16 and HPV-18, may be the cause for the development of cervical cancer. Although cervical cancer research has accomplished progress in the past, some of the most critical work is impeded by a lack of human tissue models. Likewise, research relating to ovarian cancers, uterine cancer, uterine fibroids, or endometriosis would benefit greatly from having human tissue models of the cervix, uterus, oviduct (fallopian tube), and vagina.

The cervix, uterus, oviduct, and part of the vagina of the female reproductive system are formed early in embryogenesis from Müllerian ducts, also known as paramesonephric ducts. In human embryos, a primordial gonadal ridge develops into a primitive gonad. At about the seventh week of gestation, both sexes have primordial genital ducts and a primitive gonad which develops into a cortex and a medulla. In genetic females, the cortex develops into ovaries and the medulla regresses. In contrast, the medulla develops into testes and the cortex regresses in genetic males. As development of a human embryo progresses, Müllerian ducts in males begin to regress with the secretion of Müllerian inhibiting substance (or MIS). Ganong, William F. Review of Medical Physiology, Chapter 23 "The Gonads: Development and Function of the Reproductive System", Fifteenth Edition, Appleton and Lange (1991). The Müllerian duct is either of the two paired embryonic tubes extending along the mesonephros roughly parallel to the mesonephric duct and emptying into the cloaca. In females, the upper parts of the Müllerian duct form the oviducts, while the lower parts fuse to form the uterus, cervix, and part of the vagina.

Previous work on Müllerian ducts have focused on anatomical and structural characteristics of Müllerian ducts. For example, one study revealed that the movements of Müllerian ridges and the immunohistochemical staining of Müllerian ducts in avians closely resemble that seen in human. Jacob M, et. al. Cells Tissues Organs 164(2), 63–81, (1999). In another study, human fetuses were examined by ultrasound to study the developing urogenital tracts. Lawrence W. D., et. al. American Journal of Obstetrics and Gynecology 167(1), 185–193, (1992). Other studies have focused on gene expression patterns in the developing fetus. Pellegrini M. et. al. Anat. Embryol. 196(6). 427–433, (1997). While important in their respective scopes, these studies do not provide any teachings for methods of isolating Müllerian duct-derived epithelial cells, nor do they provide any teaching for methods for culturing Müllerian duct-derived epithelial cells such that the cells retain their pluripotent potential. There are very few, if any, reports of Müllerian duct-derived epithelial cells that have been isolated and even fewer reports of Müllerian duct-derived epithelial cells that have pluripotent potential to differentiate into uterine, cervical, oviductal, and vaginal cells. Accordingly, there exists a need for the discovery of a population of Müllerian duct-derived epithelial cells as well as methods of isolating and characterizing Müllerian duct-derived epithelial cells. The invention disclosed herein fulfills these needs and discloses additional methods of use as well.

DISCLOSURE OF THE INVENTION

In one aspect, the invention relates to a population of substantially pure human Müllerian duct-derived epithelial cells that have a pluripotent capability to differentiate into oviductal, uterine, vaginal, or cervical cells.

In another aspect, the invention relates to methods of isolating a population of substantially pure human Müllerian duct-derived epithelial cells that have the pluripotent capability to differentiate into oviductal, uterine, vaginal, and cervical cells.

In yet another aspect, the invention relates to methods of maintaining a population of substantially pure human Müllerian duct-derived epithelial cells that have the pluripotent capability to differentiate into oviductal, uterine, vaginal, and cervical cells and maintaining or culturing these Müllerian duct-derived epithelial cells under culture conditions sufficient to allow the Müllerian duct-derived epithelial cells to retain their pluripotent capacity.

In still another aspect, the invention relates to methods of providing a source of immunogen to a heterologous recipient and the uses of a substantially pure population of Müllerian duct-derived epithelial cells as an immunogen.

In still another aspect of this invention, the invention relates to methods of generating a human tissue model of Müllerian duct-derived cells or cells differentiated from Müllerian duct-derived cells (i.e. oviductal, uterine, vaginal, and cervical cells) using a substantially pure population of Müllerian duct-derived epithelial cells or cell differentiated therefrom as a source of Müllerian duct-derived cells and administering the Müllerian duct-derived epithelial cells into a non-human, mammalian recipient.

In another aspect of this invention, the invention relates to methods of providing cell therapy whereby a substantially pure population of human Müllerian duct-derived epithelial cells or cell differentiated therefrom are introduced into a recipient.

In another aspect of this invention, the invention relates to methods of providing a means for developing pharmaceutical drugs wherein a substantially pure population of human Müllerian duct-derived epithelial cells is used as a source of Müllerian duct-derived biological components in which one or more of these Müllerian duct-derived biological components are the targets of the drugs that are being developed.

In another aspect of this invention, the invention relates to methods of providing bioassay development wherein a substantially pure population of human Müllerian duct-derived epithelial cells are used as a source of nucleic acids or proteins and wherein these nucleic acids or proteins are used as one or more principal components in a bioassay or the development of a bioassay.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

FIG. 2A shows staining of MTE cells for cytokeratin 19. FIG. 2B shows staining of MTE cells for cytokeratins 10, 11, and 18. FIG. 2C shows cytokeratin staining of MTE cells for cytokeratins 13 and 16. FIG. 2D shows staining of MTE cells for vimentin.

MODES FOR CARRYING OUT THE INVENTION

Figure 1:
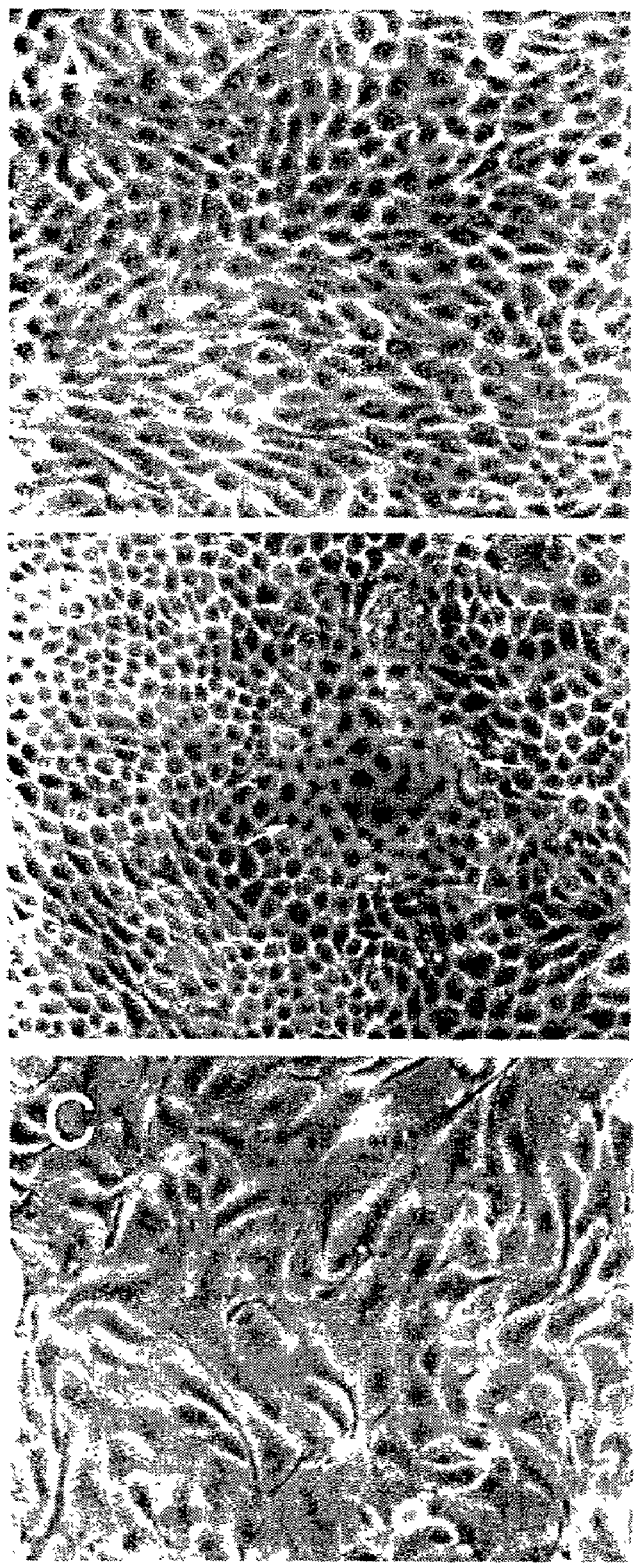
FIG. 1A shows Müllerian Tract Epithelial (MTE) cells, as seen under phase contrast microscope, as a tight epithelial cell colony.
FIG. 1B shows MTE cells, as seen under phase contrast microscope, at high density in culture when MTE cells form dome-like structures (indicated by arrows).
FIG. 1C shows MTE cells, as seen under phase contrast microscope, with smooth cell outlines and slender processes. This cell morphology resembles that seen with endometrial epithelial cell cultures.

The following detailed description of the invention is provided to aid those skilled in the art in practicing the present invention. This detailed description should not be construed to limit the present invention, as modifications of the embodiments disclosed herein may be made by those of ordinary skill in the art without departing from the spirit and scope of the present invention. Throughout this disclosure, various publications, patents, and published patent specifications are referenced by citation. The disclosure of these publications, patents, and published patents are hereby incorporated by reference in their entirety into the present disclosure.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, $2^{nd}$ edition (1989); CURRENT PROTOCOLS IN MOLECULAR BIOLOGY (F. M. Ausubel, et al. eds., (1987); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987).

Definitions

As used in the specification and claims, the singular form "a", "an" and "the" include plural references unless the context clearly dictates otherwise. For example, the term "a cell" includes a plurality of cells, including mixtures thereof.

As used in the specification and claims, the terms "Müllerian duct-derived epithelial cells", "Müllerian duct-derived cells", "Müllerian ductal cells", and "Müllerian duct cells" are used interchangeably and refer to cells derived from human Müllerian ducts. These cells are capable of dividing and have not yet committed to an essentially non-dividing stage of end differentiation. "Müllerian duct-derived epithelial cells", "Müllerian ductal cells", and "Müllerian duct cells" are derived ultimately from a paramesonephric ridge in human embryos. While both male and female embryos have Müllerian ducts, the Müllerian ducts in males regress with embryonic development and with the secretion of Müllerian inhibiting substance (MIS) while in females, the Müllerian ducts develop into oviducts, uterus, endometrium, cervix, and the upper part of a vagina.

"Müllerian tract epithelial cells" and "MTE cells" are used interchangeably herein and refer to Müllerian duct-derived epithelial cells that are in culture under standard in vitro cell conditions.

As used herein, "paramesonephric duct" and "Müllerian duct" are used interchangeably. "Paramesonephric duct" and "Müllerian duct" are derived from a primordial genital duct in the early stages of embryonic development.

"Pluripotent" and "multipotent" are used interchangeably throughout and refer to a stage where a cell can still become one of a plurality of cells but can no longer become any type of cell in the body (i.e. totipotent).

As used herein, "pre-determined Müllerian duct-derived" refers to a stage of development of a multipotent cell that is beyond the stage of being part of the primordial gonadal ridge and before the stage of terminally differentiated Müllerian duct-derived cells (such as mature oviductal, uterine, cervical, and vaginal cells). Cells which are "pre-determined Müllerian duct-derived" are committed to becoming Müllerian duct-derived cells but have not begun to develop into terminally differentiated Müllerian duct-derived cells yet. Different factors cause pre-determined Müllerian duct-derived cells to begin differentiating. Non-limiting examples include exposure to hormones (i.e. estrogen, progesterone, leutinizing hormone, etc.), cell-to-cell contact with surrounding tissue (i.e. mesenchymal tissue), and microenvironment of the cells.

An "antibody" is an immunoglobulin molecule capable of binding an antigen. As used herein, the term encompasses not only intact immunoglobulin molecules, but also antiidiotypic antibodies, mutants, fragments, fusion proteins, humanized proteins and modifications of the immunoglobulin molecule that comprise an antigen recognition site of the required specificity.

The term "antigen" is a molecule which can include one or a plurality of epitopes to which an antibody can bind. An antigen is a substance which can have immunogenic properties, i.e., induce an immune response. Antigens are considered to be a type of immunogen. As used herein, the term "antigen" is intended to mean full length proteins as well as peptide fragments thereof containing or comprising one or a plurality of epitopes.

The terms "surface antigens" and "cell surface antigen" are used interchangeably herein and refer to the plasma membrane components of a cell. These component include, but are not limited to, integral and peripheral membrane proteins, glycoproteins, polysaccharides, lipids, and glycosylphosphatidylinositol (GPI)-linked proteins. An "integral membrane protein" is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface by noncovalent interaction with other membrane proteins. GPI-linked proteins are proteins which are held on the cell surface by a lipid tail which is inserted into the lipid bilayer.

The term "monoclonal antibody" as used herein refers to an antibody composition having a substantially homogeneous antibody population. It is not intended to be limited as regards to the source of the antibody or the manner in which it is made (e.g. by hybridoma or recombinant synthesis). Monoclonal antibodies are highly specific, being directed against a single antigenic site. In contrast to conventional (polyclonal) antibody preparations which typically include different antibodies directed against different determinants (epitopes), each monoclonal antibody is directed against a single determinant on the antigen.

"A population of monoclonal antibodies" refers to a plurality of heterogeneous monoclonal antibodies, i.e., individual monoclonal antibodies comprising the population may recognize antigenic determinants distinct from each other.

"Immunogen" refers to any substance that induces an immune response. A substance that is an immunogen is described as being "immunogenic". Induction of immune response includes but is not limited to activation of humoral responses (e.g. producing antibodies) or cellular responses (e.g. priming cytotoxic T cells), inflammatory responses (e.g. recruitment of leukocytes), and secretion of cytokines and lymphokines.

The term "heterologous" as applied to a cell used for immunization or transplantation means that the cell is derived from a genotypically distinct entity from the recipient. For example, a heterologous cell may be derived from a different species or a different individual from the same species as the recipient. An embryonic cell derived from an individual of one species is heterologous to an adult of the same species. "Heterologous" as applied to a recipient means that the recipient is a genotypically distinct entity from the source of the cells that are being introduced into the recipient.

"Explant" refers to Müllerian duct tissues taken out of a human fetus. Generally, explants are used as a source of Müllerian duct-derived cells. Isolating the cells from the explant can be accomplished by several methods. One method is to place the Müllerian duct tissue explant, either whole tissue or cut in smaller pieces, in a basal defining media and allow the cells of the Müllerian duct to naturally migrate out of the solid tissue mass into the media. Another method is to subject the Müllerian duct tissue to enzymatic digestion or to mechanical forces that forces cells away from the solid tissue.

A cell is of "ectodermal", "endodermal" or "mesodermal" origin, if the cell is derived, respectively, from one of the three germ layers—ectoderm, the endoderm, or the mesoderm of an embryo. The ectoderm is the outer layer that produces the cells of the epidermis, and the nervous system. The endoderm is the inner layer that produces the lining of the digestive tube and its associated organs. The middle layer, mesoderm, gives rise to several organs, including but not limited to heart, kidney, mesothelium, and gonads), connective tissues (e.g., bone, muscles, tendons), and the blood cells.

The terms "medium", "cell culture medium", and "culture medium" are used interchangeably. The terms refer to the aqueous microenvironment in which the mammalian cells are grown in culture. The medium comprises the physicochemical, nutritional, and hormonal microenvironment.

A cell culture medium is "essentially serum-free" when the percentage by volume of serum in the medium does not mask antigenic sites or antibody binding sites on cell surfaces. The term "essentially serum-free" generally applies when the cell culture medium comprises less than about 50% serum (by volume), preferably less than about 25% serum, even more preferably less than about 5% serum, and most preferably less than about 0.1% serum.

A cell surface is "substantially free of serum biomolecules" when at least about 50% of the Müllerian tract epithelial cell surfaces, more preferably at least about 75% of the Müllerian tract epithelial cell surfaces, even more preferably at least about 90% of the Müllerian tract epithelial cell surfaces, and most preferably at least about 95% of the Müllerian tract epithelial cell surfaces do not have serum biomolecules derived from serum binding to the cell surface such that antigenic sites or antibody binding sites are bound or are unavailable for antigenic recognition by an antibody or a portion of an antibody. Cell surface can determined by measuring the cell size, either by microscopy or flow cytometry. For example, synthetic beads of various known sizes are commonly used for calibration in flow cytometry. A small quantity of calibrated bead may be mixed with MTE cells and the resultant population is analyzed by flow cytometry. MTE cells can then be compared with the size of the calibrated beads. Calculations of cell surface amount can be accomplished since the sizes of the beads are known.

As used herein, a "substantially pure" population of Müllerian tract epithelial cells is a population of cells that is comprised at least about 85% Müllerian tract epithelial cells, preferably at least about 90%, and even more preferably about 95% or more.

A "defined medium," "basal cell-sustaining medium," "nutrient medium", and "basal nutrient medium" are used interchangeably herein and refer to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cystine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, "conditioned media" refers to culture media, free of intact cells, in which MTE cells have been grown. Müllerian duct-derived cells grown in nutrient media may release factors which promote the continued survival, growth, and maintenance of pre-existing state of pre-differentiation of the Müllerian tract epithelial cells. Conditioned media may be used to reconstitute a cell pellet or added to cells already existing in culture plates. Conditioned media may also be used alone or to supplement nutrient media being used to feed Müllerian duct-derived cells. Since conditioned media is derived from nutrient media and nutrient media, as disclosed herein, is essential serum-free, conditioned media is also essentially serum-free.

"Standard incubation conditions" refers to the physicochemical conditions in an incubator designed for tissue culture in which cells are placed. Generally, the standard incubation conditions are about 37 degrees Celsius and about 5% $CO_2$ content with humidification. All tissue culture techniques and equipment should be performed under sterile conditions.

"Müllerian tract epithelial cell aggregates", "MTE aggregates", and "MTE cell spheres" are used interchangeably throughout and refer to a monolayer mass of Müllerian tract epithelial cells that are patches of cells in close physical proximity and have cell-to-cell contact.

A "grafting recombinant", as used herein, refers to the combined unit of Müllerian tract epithelial cell aggregates placed with mesenchymal tissue. Mesenchymal tissue can be of Müllerian duct-derived or non-Müllerian duct-derived origin. Mesenchymal tissue can be from a species heterologous to the graft recipient. Mesenchymal tissue can also be from a species heterologous to the source of Müllerian tract epithelial cells. Grafting recombinants can be incubated on substrate, preferably a soft, biological substrate (e.g. agar) for a period ranging from 1 hour to 96 hours, more preferably between about 6 hours to 48 hours, and even more preferably, overnight with an incubation period of about 24 hours.

"Serum", as used herein, refers to the fluid phase of mammalian blood that remains after blood is allowed to clot.

"Serum biomolecules", as used herein, refers to biological compositions found in serum. Examples include, but are not limited to, albumin, $\alpha 1$-globulin, $\alpha 2$-globulin, $\beta$-globulin, and $\gamma$-globulin. Serum biomolecules can include biological compositions, whole or partial, that are either naturally found in serum or derived from processing and handling of serum.

The terms "mammals" or "mammalian" refer to warm blooded vertebrates which include but are not limited to humans, mice, rats, rabbits, simians, sport animals, and pets.

Isolation and Maintenance of Millerian Tract Epithelial Cells

Müllerian tract epithelial cells of this invention are isolated from human fetal Müllerian duct-derived tissue. The age of the fetus is between about week 1 and about week 40, preferably between about week 8 and about week 30, and even more preferably between about week 17 and about week 25. The Müllerian duct-derived tissue can be identified by gross anatomy, outward appearance, and location within the fetus. The appearance distinguishing a Müllerian duct is either of two paired embryonic tubes extending along the mesonephros roughly parallel to the mesonephric duct and emptying into the cloaca in the female, the upper parts of the ducts form the uterine tubes while the lower fuse to from the uterus and part of the vagina. Once identified, fetal Müllerian duct-derived tissue is separated from excess connective tissue, washed with basal media, and then microdissected. The purpose of microdissection is to divide the solid tissue mass into smaller parts of the whole tissue mass so that the basal nutrient media has greater access to Müllerian duct-derived cells within the tissue pieces and/or to separate Müllerian duct-derived cells from Müllerian duct tissue mass. Non-limiting examples of microdissection include devices that render mechanical shearing forces (i.e. homogenizer, mortar and pestle, blender, etc.), devices that render cuts or tears (i.e. scalpel, syringes, forceps, etc.), or ultrasonic devices. Alternatively, another method of microdissecting fetal Müllerian duct-derived tissue is the use of enzyme treatment. Various enzyme treatments used to microdissect tissue are well known in the art. One method includes the use of collagenase-dispase to digest partially sheared Müllerian duct-derived tissue in a buffered medium that will sustain viability of cells isolated from the Müllerian duct-derived tissue. The amount of enzyme will depend on the age of the fetus and the mass of the Müllerian duct tissue. In one embodiment, enzyme treatment with collagenase-dispase may lower the overall cell yield. Accordingly, the amount of enzyme used would be reduced or not used at all. In other embodiments, enzyme treatment may increase overall cell yield. Accordingly, enzyme treatment may be used alone or in combination with microdissection methods. A wide variety of basal cell-sustaining media that can be used to keep the pH of the liquid in a range that promotes survival of Müllerian tract epithelial cells and to provide additional volume of liquid within which the enzymatic digestion can occur. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), and Iscove's Modified Eagle's Medium (IMEM). In addition, any of the basal nutrient media described in Ham and Wallace (1979) *Meth. Enz.,* 58:44, Barnes and Sato (1980) *Anal. Biochem.,* 102: 255, or Mather, J. P. and Roberts, P. E. (1998) "Introduction to Cell and Tissue Culture", Plenum Press, New York can also be used.

Small pieces of Müllerian duct tissue are then placed in a basal cell-sustaining media. A variety of basal cell-sustaining media is available for use. Examples include, but are not limited to, Ham's F12 medium, RPMI-1640, and CMRL-1066. For more optimal conditions to promote Müllerian duct epithelial cell survival and growth, a variety of nutrients may be added to supplement the basal media. Examples include, but are not limited to, insulin, transferrin, $\alpha$-tocopheral, and aprotinin. In a preferred embodiment, the following amounts of nutrients are used to promote Müllerian duct epithelial cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 0.1 µg/ml $\alpha$-tocopherol and not more than about 1 mg/ml α-tocopherol, more preferably about 5 µg/ml α-tocopherol; and at least about 1 µg/ml aprotinin and not more than about 100 µg/ml aprotinin, more preferably about 5 µg/ml aprotinin.

Müllerian duct epithelial cells migrate out the Müllerian duct tissue into the media in which the Müllerian duct tissue is placed. In one embodiment, the Müllerian duct epithelial cells migrate out of the Müllerian duct tissue into the media in aggregate form. In another embodiment, the Müllerian duct epithelial cells migrate out of the Müllerian duct tissue into the media in the form of single cells. In another embodiment, the Müllerian duct epithelial cells that migrate out of the Müllerian duct tissue are no longer imbedded in the Müllerian duct tissue but are loosely associated with the tissue. Müllerian duct-derived cells are then resuspended in a basal cell-sustaining media. The Müllerian duct epithelial cells can be grown in tissue culture containers (i.e. flasks, plates, etc.) that are either uncoated or coated with different substrates. Non-limiting examples of substrates that may be used include fibronectin, laminin, collagen, polylysine, nitrocellulose, nylon, and polytetrafluoroethylene. In one embodiment, Müllerian duct epithelial cells are grown on laminin-coated tissue culture containers in the preferred nutrient media described above. In another embodiment, Müllerian duct epithelial cells are grown in uncoated tissue culture containers in the preferred nutrient media described above. The size of the tissue culture containers is proportional to the amount of Müllerian duct tissue being placed within the containers. A skilled artisan may determine the correct size of the tissue culture containers by a stepwise increment of Müllerian duct tissue placed within the tissue culture containers. When the Müllerian duct tissue is first placed within the tissue culture containers, the media is generally clear in overall turbidity. As Müllerian duct-derived cells migrate out and away from the Müllerian duct tissue pieces, the media will become more opaque and more turbid. At the point where the media is highly turbid because of the increasing amount of Müllerian duct-derived cells migrating from the Müllerian duct tissue or because of Müllerian duct-derived cell growth, more nutrient media is placed in the tissue culture containers to replenish the nutrients consumed by the Müllerian duct cells. In the alternative, when the media becomes turbid with increasing amounts of Müllerian duct epithelial cells, a small amount of cells may be removed from the tissue culture containers and checked for cell viability, for example, with trypan blue staining. Tissue culture containers that have been overrun with too many cells will begin to show decreased cell viability. The skilled artisan may then transfer the contents of the tissue culture containers to other containers of a larger size (e.g. greater cubic volume) to accommodate the increasing amount of cells. In one embodiment, the entire content of the tissue culture container is transferred to another container of a larger cubic volume. In another embodiment, the Müllerian duct cell suspension is split into several separate tissue culture containers with fresh nutrient media (also known as "subculturing"). In this manner, a substantially pure population of Müllerian duct cells can be obtained.

The Müllerian duct cells in culture or Müllerian tract epithelial (MTE) cells may be grown in tissue culture containers (e.g. flasks, plates, etc.) that are either uncoated or coated with different substrates. Non-limiting examples of substrates that may be used include fibronectin, laminin, collagen, polylysine, nitrocellulose, nylon, and polytetrafluoroethylene. MTE cells form monolayers when grown with or without substrate in the preferred nutrient media. In one embodiment, MTE cells grown in uncoated tissue culture flasks form a monolayer. In another embodiment, MTE cells at high density in the preferred nutrient media form enclosed dilated cysts which float freely in the preferred nutrient medium. In still another embodiment, MTE cells form monolayer patches or monolayer aggregates in the tissue culture container. In yet another embodiment, MTE aggregates adhere to the surface of tissue culture containers and proliferate as a colony of monolayer cells. These colonies may be subcultured to propagate MTE cells. Various methods can be used to subculture MTE cell colonies. One method is enzymatic treatment to detach the colonies from the sides of the plastic tissue culture flasks. In a more preferred embodiment, an enzyme such as collagenase-dispase is used in an effective amount to dissociate MTE aggregates from the sides of the tissue culture flask while leaving the cells in aggregate formation. An effective amount is at least about 10%, more preferably at least about 1%, and most preferably at least about 0.1% collagenase-dispase by volume. After detachment of MTE colonies from the sides of the tissue culture flask, the enzyme is washed away with a basal media, preferably the nutrient media disclosed herein, and the MTE colonies are placed in new flasks with a nutrient media, preferably the nutrient media disclosed herein. The entirety of MTE colonies may be placed in a single tissue culture flask to which nutrient media is added or in an alternative, a portion of the MTE colonies is placed in a single tissue culture flask to which nutrient media is added. By subculturing in this manner, a confluent cell culture may be obtained in at least about two months, more preferably at least about one month, and most preferably at least about two to three weeks. In an alternative, growth factors such as basic fibroblast growth factor (FGF) and forskolin may be added in stepwise increments to stimulate proliferation. In some embodiments, the addition of FGF and/or forskolin promotes a greater rate of proliferation and does not decrease the life span of the MTE cells. Accordingly, the addition of FGF and/or forskolin may be used when a greater proliferation rate is desired by a skilled artisan. In other embodiments, the addition of FGF and/or forskolin promotes a greater rate of proliferation and decreases the life span of the MTE cells. Accordingly, a skilled artisan may determine if an increased number of MTE cells is desired over longevity of MTE cells depending on his needs.

The frequency of feeding Müllerian tract epithelial cells is dependent on the rate of nutrient metabolism of MTE cells. The higher rate of nutrient metabolism, the more frequent MTE cells need to be fed. Generally, media acidity will increase as cells metabolize nutrients in the media. Some nutrient media (e.g. RPMI-1640, DMEM, EMEM, etc.) have media colors that indicate the acidity such that media that is highly acidic will turn bright shades of pink. Nutrient media can then be added to bring acidity of the existing media to an acidity that will sustain life and promote growth of the MTE cells. Alternatively, a small portion of MTE cells may be removed from the tissue culture container and assessed for cell viability, for example, with trypan blue staining. If the nutrient media has been metabolized, cell viability will be poor (i.e. less than 50%). In one embodiment, Müllerian tract epithelial cells may be fed by replacing the entirety of the old nutrient media with new nutrient media. In another embodiment, Müllerian tract epithelial cells may be fed with conditioned media in which these cells were grown. Because the claimed Müllerian tract epithelial cells are unique to this invention and will secrete factors specific to these cells, the conditioned media derived from the Müllerian tract epithelial cells are also unique. A frequency of feeding that is preferable for promoting the survival and growth of Müllerian tract epithelial cells is about once a week. The Müllerian tract epithelial cells of this invention can be passaged multiple (about 4–5) times without senescence and without inducing differentiation of these Müllerian tract epithelial cells into terminally differentiated uterine, cervical, vaginal, or oviductal cells.

Characterization of Müllerian Tract Epithelial Cells

The population of Müllerian tract epithelial cells of this invention isolated in the manner disclosed herein have several defining characteristics. First, the Müllerian tract epithelial cells are at a stage that can be described as "pre-determined Müllerian duct-derived". The Müllerian tract epithelial cells of this invention have the capacity to become either uterine, cervical, vaginal, or oviductal cells. Identification of Müllerian tract epithelial cells may be accomplished by morphology or specific markers or a combination of both techniques. Morphology of MTE cells is characterized by monolayer formation of polygonal or ovoid shaped cells in close proximity to each other, with cell-to-cell contact, and growth in tight colonies. When MTE cells are at high density in tissue culture containers, they can form dome-like structures. The formation of dome-like structures is an unique property for glandular epithelial cells. The formation of dome-like structures indicate that MTE cells form occlusive junctions or tight junctions between the adjacent cells. Occlusive junctions can be visualized by conventional or freeze fracture electron microscopy or alternatively, by staining by markers to occlusive junctions (i.e. zona occludens proteins ZO1, ZO2, etc.). In addition to the formation of dome-like structures, MTE cells can also secrete protein into the lumen of the domes. The protein may be visualized by staining with dyes (i.e. hematoxylin, eosin, etc.) Other morphology that MTE cells can present is an epithelial cell type with smooth outline and slender processes, similar to that seen with endometrial epithelial cell cultures from human adult endometrium.

Markers that can be used to detect MTE cells include but are not limited to cytokeratins (CK) 1, 5, 6, 7, 8, 10, 11, 13, 15, 16, 18, and 19 and vimentin on MTE cell surfaces. These cell surface markers are assessed by employing antibodies specific for CK and vimentin. Examples of antibodies that may be used include but are not limited to: anti-cytokeratin (CK) antibodies clone 4.62, clone 8.12, clone 8.13 from Sigma Chemical Co. and anti-vimentin antibodies clone 13.2 from Sigma Chemical Co. Anti-CK antibodies and anti-vimentin antibodies can be used in either direct or indirect staining of MTE cells in immunohistochemistry or by flow cytometry.

MTE cells of this invention is also characterized by expression of HOX genes. HOX genes are vertebrate homologues of homeotic selector genes that define positional values along the anterior-posterior axis in Drosophila. Hoxa9 gene expression is restricted to fallopian tube (oviduct), Hoxa10 gene expression is restricted to endometrial expression, and Hoxa11 gene expression is restricted to endocervical epithelial cells. Taylor H. S. et. al. Biology of Reproduction 57, 1338–1345 (1997). MTE cells are isolated and cultured using the methods disclosed herein and total RNA is extracted from MTE cells and subjected to reverse transcriptase polymerase chain reaction (RT-PCR) using primers specific to Hoxa9, Hoxa10, Hoxa11 gene sequences.

MTE cells of this invention may also be characterized by their sensitivity to different hormones or compounds. Müllerian Inhibition Substance (MIS) is known to cause regression of Müllerian ducts in male embryos. Application of MIS to MTE cells can cause several cellular morphological effects that may be observed by phase contract microscopy. Alternatively, expression of MIS receptors may be modulated by exposure to MIS. Receptor expression may be assessed by flow cytometry with MIS receptor-specific antibodies. Hormones such as progesterone, estrogen, or luteinizing hormone (LH) can affect MTE cells. In female embryos, exposure to progesterone and estrogen causes differentiation of the Müllerian duct into uterus, oviduct, cervix, and part of a vagina. Upon exposure to LH, MTE cells may be monitored for cell morphological effects by phase contract microscopy. Alternatively, proliferation assay may be used to monitor cell growth in response to LH. Yet in another alternative, MTE cells can be stained for markers specific for uterine, cervical, oviductal, or vaginal tissues and analyzed by immunohistochemistry or flow cytometry.

Müllerian tract epithelial cells of this invention are maintained in serum-free media at a stage that can be described as pre-determined Müllerian duct-derived state. Basal cell-sustaining media or the preferred nutrient media disclosed herein or conditioned media may be used to culture the Müllerian tract epithelial cells in vitro. Müllerian tract epithelial cells of this invention have the capacity to be passaged multiple times in the preferred serum-free nutrient media disclosed herein. Multipotency is retained during each passage and at any point after each passage, Müllerian tract epithelial cells of this invention can differentiate into functional Müllerian duct-derived cells. In addition, at any point after each passage, Müllerian tract epithelial cells may be used as an immunogen, for cell therapy, for bioassays, to establish a human Müllerian duct-derived model, or for drug discovery and/or development as disclosed herein.

Another characteristic of the Müllerian tract epithelial cells of this invention is the capacity to differentiate into uterine, cervical, oviductal, or vaginal cells upon transplantation under kidney capsule of a recipient mammal. Müllerian tract epithelial cells are grown in monolayers and then combined with mesenchymal tissue and placed under a kidney capsule of a recipient mammal. Preferably, human Müllerian tract epithelial cell aggregates are combined with rat urogenital mesenchymal tissue and placed under the kidney capsule of a recipient mammal. A portion of the transplant may be removed for analysis using the markers, morphology, or a combination thereof to identify the Müllerian duct-derived cells and cell differentiated therefrom.

Uses of Müllerian Tract Epithelial Cells

Uses as an Immunogen

A use for Müllerian tract epithelial cells is as an immunogen. As disclosed in this invention, the unique serum-free culturing conditions allow the cell surfaces of the Müllerian tract epithelial cells to remain free of serum proteins or serum biomolecules that may bind to the surface. A potential problem of antigenic sites that may be "masked" with binding by serum biomolecules is avoided by using the disclosed serum-free isolation and culturing techniques. Accordingly, a panel of antibodies may be generated to newly available antigens that were "masked" when using culture conditions containing serum. Müllerian tract epithelial cells isolated and cultured with the methods disclosed herein can be used as an immunogen that is administered to a heterologous recipient. Administration of MTE cells as an immunogen can be accomplished by several methods. Methods of administrating MTE cells as immunogens to a heterologous recipient include but are not limited to: immunization, administration to a membrane by direct contact such as swabbing or scratch apparatus, administration to mucous membrane by aerosol, and oral administration. As is well-known in the art, immunization can be either passive or active immunization. Methods of immunization can occur via different routes which include but are not limited to intraperitoneal injection, intradermal injection, local injection. The subjects of immunization may include mammals such as mice. The route and schedule of immunization are generally in keeping with established and conventional techniques for antibody stimulation and production. While mice are employed in this embodiment, any mammalian subject including humans or antibody producing cells therefrom can be manipulated according to the processes of this invention to serve as the basis for production of mammalian hybridoma cell lines. Typically, mice are inoculated intraperitoneally with an immunogenic amount of the MTE cells and then boosted with similar amounts of the immunogen. In an alternative, cells grown on non-biological membrane matrix, are surgically implanted intraperitoneally into the host mammal. Lymphoid cells, preferably spleen lymphoid cells from the mice, are collected a few days after the final boost and a cell suspension is prepared therefrom for use in the fusion.

Hybridomas are prepared from the lymphocytes and immortalized myeloma cells using the general somatic cell hybridization technique of Kohler, B. and Milstein, C. (1975) *Nature* 256:495–497 as modified by Buck, D. W., et al., (1982) In Vitro, 18:377–381. Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

In this manner, a panel of novel antibodies to cell surface antigen specific to Müllerian tract epithelial cells can be generated using the Müllerian tract epithelial cells of this invention. Once monoclonal antibodies to cell surface antigens on Müllerian tract epithelial cells are made by the method disclosed herein, the antibodies have several uses. The antibodies may be sequenced and cloned for purposes of generating recombinant antibodies or humanized antibodies. Other uses of Müllerian tract epithelial cell-specific antibodies include, but are not limited to, biological testing and purification (i.e. isolating Müllerian duct-derived epithelial cells, for example by flow cytometry or panning), therapeutic uses (i.e. promoting or arresting cell growth by binding of antibody to target cell or promoting or arresting growth of a cell mass by binding of antibody to target cell), biological markers (i.e. identification of other Müllerian duct-derived or non-Müllerian duct-derived cells), and clinical diagnosis (i.e. identification of cancerous uterine, cervical, oviduct, or vaginal cells).

Another use as an immunogen is to modulate overall immune response in a heterologous recipient. As is well-documented in the art, foreign substances such as cells or organs introduced into a heterologous recipient may induce a variety of immune responses. The immune responses can be in the form of rejection (e.g. in organ transplantation), T cell activation (e.g. cross-priming), anergy, or tolerance. The overall immune response can be systemic or localized. In the case where a localized immune response is desired, for example in the gonadal region, an immunogen such as Müllerian tract epithelial cells is introduced into the gonadal region in an effective amount. Effective amount can be determined in a stepwise fashion in which increasing amounts of Müllerian tract epithelial cells are introduced into a heterologous recipient and the subsequent immune response is monitored. Overall immune response (e.g. antibody production, cytokine production, T cell proliferation, anergy, tolerance, etc.) may be monitored by a number of methods including but not limited to ELISA, proliferation assays, flow cytometry with cell surface markers, and immunohistochemistry.

Use of Müllerian Tract Epithelial Cells for Drug Discovery

Another use of Müllerian tract epithelial cells is related to drug discovery. Since the pre-determined multipotent Müllerian tract epithelial cell population has not been isolated and cultured in the disclosed manner, the Müllerian tract epithelial cell population may secrete proteins that have not been heretofore discovered or characterized. Previous culturing techniques using serum may inhibit the secretion of proteins. Alternatively, proteins may change in function, conformation, or activity as they are being secreted and interacting with serum biomolecules. Proteins secreted by Müllerian tract epithelial cells have minimal interference from serum biomolecules and thus, may be more physiologically and topologically accurate. Therefore, proteins secreted by Müllerian tract epithelial cells may be used as targets for drug development. In one embodiment, drugs can be made to target specific proteins on Müllerian tract epithelial cells and/or cells differentiated therefrom in vivo. Binding of the drug may promote differentiation of the Müllerian tract epithelial cells into uterine, cervical, oviductal, and vaginal cells. This approach may be useful when neogenesis of uterine, cervical, oviductal, or vaginal cells are desired, for example in cases of partial and complete hysterectomies or tissue damage.

Uses of Müllerian Tract Epithelial Cells for Cell Therapy

In another use, Müllerian tract epithelial cell lines are used for cell therapy. Transplantation of Müllerian tract epithelial cells and cells derived therefrom is one such example of cell therapy. In cases where mature gonadal cells such as uterine, cervical, oviductal, endometrial, and-vaginal cells are desired, Müllerian duct-derived cells of this invention are useful because of their capability to differentiate into uterine, cervical, oviductal, endometrial, and vaginal cells. To practice this use, Müllerian tract epithelial cells are isolated and cultured in serum-free, nutrient-defined media using the methods disclosed. Müllerian tract epithelial cells are grown on tissue culture containers, either uncoated or coated with substrate, to obtain Müllerian tract epithelial cell monolayer aggregates. Müllerian tract epithelial cell aggregates are grown under standard incubation conditions at least about 1 cell cycle passage, more preferably for at least about 2 cell cycle passage, most preferably at least about 3 cell cycle passages. Müllerian cell aggregates can then be administered to a recipient and allowed to differentiate. In an alternative, Müllerian cell aggregates can be used as cellular carriers of gene therapy wherein Müllerian cells are transfected with one or more genes and enclosed in a delivery device and then administered to a recipient. In another embodiment, Müllerian cell aggregates are placed under a kidney capsule and allowed to differentiate into uterine, cervical, oviductal, and vaginal cells. In another embodiment, Müllerian cell aggregates are used in a device which contains cells and limits access from other cells (i.e. Theracyte®) to limit immune system responses.

Uses of Müllerian Tract Epithelial Cells to make Human Tissue Models

Another use for Müllerian tract epithelial cells is to create human tissue models in non-human mammals. Müllerian tract epithelial cell aggregates are placed on top of mesenchymal tissue to form grafting recombinants. The mesenchymal tissue may be either Müllerian duct-derived or non-Müllerian duct-derived tissue and may be derived from a different species from which Müllerian tract epithelial cells are isolated. In a working example, human Müllerian tract epithelial cells are placed on top of rat mesenchymal urogenital tissue to form a graft recombinant. A skilled artisan may determine the optimal combination in a stepwise fashion, by first isolating human Müllerian tract epithelial cells using the methods disclosed herein and then combining with mesenchymal tissue from different organs. In some embodiments, a different species, e.g. rat, is used as a source for mesenchymal tissue in combination with human Müllerian tract epithelial cells. The use of heterologous species allows human-specific markers to be used to determine the identity of differentiated Müllerian duct-derived cells. The likelihood of false positives is reduced if rat mesenchymal tissue is used. Likewise, the use of urogenital mesenchymal tissue over Müllerian duct-derived mesenchymal tissue reduces the likelihood of false positives in identifying differentiated Müllerian duct-derived cells. A graft recombinant comprising Müllerian tract epithelial cell spheres placed on mesenchymal tissue is cultured on a soft substrate, such as agar, preferably about half a day to about 3 days, more preferably about one day, and then placed under the kidney capsule of a recipient mammal. Possible recipient mammals include but are not limited to mice and rats. Typically in graft situations, donor tissue is vulnerable to attack by the recipient's immune system. To alleviate graft rejection, several techniques may be used. One method is to irradiate the recipient with a sub-lethal dose of radiation to destroy immune cells that may attack the graft. Another method is to give the recipient cyclosporin or other T cell immunosuppressive drugs. With the use of mice as recipient mammals, a wider variety of methods are possible for alleviating graft rejection. One such method is the use of an immunodeficient mouse (nude or severe combined immunodeficiency or SCID). In a working example, human Müllerian tract epithelial cell spheres are placed on rat urogenital mesenchymal tissue and placed under the kidney capsule of an immunodeficient mouse. The graft recombinant remains in the recipient for about 1 week to about 52 weeks, preferably about 5 weeks to about 40 weeks, and even more preferably about 6 weeks to about 8 weeks before the grafts are harvested and analyzed for Müllerian tract epithelial cell differentiation. In some cases, a small portion of the graft is needed for analysis. Markers specific for the MTE cells and cells derived therefrom as disclosed herein may be utilized in an immunohistochemical analysis. In addition, a combination of one or more of these markers may be used in combination with cell morphology to determine the efficacy of the transplantation.

In one embodiment, human Müllerian duct-derived model can be generated in a SCID (severe combined immunodeficiency) mouse. This human Müllerian duct-derived model can be made by utilizing the human Müllerian tract epithelial cells isolated and cultured with methods disclosed herein and using the human Müllerian tract epithelial cells to make graft recombinants. Graft recombinants are then placed under the kidney capsule of mice. After about 1 to 10 weeks, preferably about 6 to 8 weeks after implantation under the kidney capsule, the graft or portion thereof is harvested and analyzed by immunohistochemistry. Cell surface markers on Müllerian duct-derived cells that may be used include, but are not limited to, CK 1, 5, 6, 7, 8, 10, 11, 13, 15, 16, 18, and 19 and vimentin. The anti-CK antibodies or anti-vimentin antibodies disclosed herein are used to analyze the efficacy of the tissue model system. Alternatively, markers specific for receptors in differentiated cells of Müllerian duct-derived tissue such as estrogen receptor and progesterone receptor are used. Yet another way to assess the results of Müllerian tract epithelial cell differentiation is by morphology. Müllerian tract epithelial cells have the appearance of polygonal or ovoid shape while the differentiated cell types have the morphology consistent with that of epithelial cells, which is well-known to those of ordinary skill in the art. Morphology can be combined with cell surface markers for a more complete assessment.

Uses of Müllerian Tract Epithelial Cells in Bioassays

The Müllerian tract epithelial cells disclosed herein can be used in various bioassays. In one use, the Müllerian tract epithelial cells are used to determine which biological factors are required for differentiation. By using the Müllerian tract epithelial cells in a stepwise fashion in combination with different biological compounds (such as hormones, specific growth factors, etc.), one or more specific biological compounds can be found to induce differentiation to uterine cells. Employing the same stepwise combinations, one or more specific biological compound can be found to induce differentiation to oviduct cells and likewise for cervical and vaginal cells. Other uses in a bioassay for Müllerian tract epithelial cells are differential display (i.e. mRNA differential display) and protein-protein interactions using secreted proteins from Müllerian tract epithelial cells. Protein-protein interactions can be determined with techniques such as yeast two-hybrid system. Proteins from Müllerian tract epithelial cells can be used to identify other unknown proteins or other cell types that interact with Müllerian tract epithelial cells. These unknown proteins may be one or more of the following: growth factors, hormones, enzymes, transcription factors, translational factors, and tumor suppressors. Bioassays involving Müllerian tract epithelial cells and the protein-protein interaction these cells form and the effects of protein-protein or even cell-cell contact may be used to determine how surrounding tissue, such as mesenchymal tissue, contributes to Müllerian tract epithelial cell differentiation.

The following examples provide a detailed description of the isolation, characterization, and use of Müllerian tract epithelial cells. These examples are not intended to limit the invention in any way.

EXAMPLES

Example 1

Isolation of Müllerian Tract Epithelial Cells

Human fetal Müllerian duct tissue of gestational age between 17 to 25 weeks were obtained from Advanced Bioscience Research at Alameda county, California. As soon as the tissues arrived, Müllerian ducts were cleaned of excess connective tissues, and cut into small segments with a razor blade or a pair of scissors under dissecting a microscope.

The segments of the Müllerian ducts from each sample were plated in a T75 tissue culture flask. The culture medium was serum free F12/DMEM supplemented with insulin (10 μg/ml), transferrin (10 μg/ml), α-tocopherol (5 μg/ml), and aprotinin (5 μg/ml) at 37° C. and 5% $CO_2$. No attachment factor was added. The epithelial cells in the segments of the ducts proliferated, emigrated, and became attached to the plastic surface during the first week of primary culture. Some of the segments formed enclosed dilated cysts floating in the culture medium. Most of the tissue segments remained in suspension. The epithelial cells that attached to flask proliferated to form large colonies. The size of the colonies reached about 1–2 cm in diameter in about 2 weeks. At that time, the cells could be subcultured for propagation.

The colonies of MTE cells were treated with 0.1% (by volume) collagenase-dispase. This enzyme mixture detached the cells from the plastic surface while keeping the cells in small monolayer aggregates. After the enzyme was washed away with nutrient medium, the MTE cells were plated in nutrient medium at 1:10 splits. The plating efficiency was low, but a fraction of cells became attached in the first week after subculture and give a confluent cell culture within 2–3 weeks. The culture medium was replenished each week. Basic fibroblast growth factor (FGF) and forskolin could stimulate the cell proliferation, but the growth factors appeared to shorten the life span of the cells. The cells were passaged in this way for 4 to 5 passages.

Example 2

Characterization of Müllerian Tract Epithelial Cells

Under phase contrast microscope, the colonies of cells grown in the primary culture were identified as all epithelial cells based on morphology. The cells kept in close contact to each other. The cell morphology exhibited by MTE cells were of two types. One type was a tight epithelial cell colony (shown in FIG. 1A). These MTE cells underwent active cell division. The MTE cells appeared to be small. At high density, the MTE cells tend to form dome-like structures (shown in FIG. 1B, indicated by arrows). The dome-like structures indicated that the MTE cells formed occlusive junctions between the adjacent cells. In addition, MTE cells secreted protein into the hollow lumen of the domes. In addition, the cells could form a second layer of round cells on the top of the bottom layer that attached to the plastic surface at high density.

The other type of morphology observed was MTE cells with a smooth outline with slender processes (shown in FIG. 1C). This cell morphology was also observed in endometrial epithelial cell cultures derived from adult human endometrium. This was probably due to the fact that Müllerian duct give rise to many types of epithelial cells (i.e. oviduct, uterus, vagina, and cervix).

Example 3

Immunohistochemistry Staining of MTE Cells for Cytokeratins and Vimentin

Figure 2:
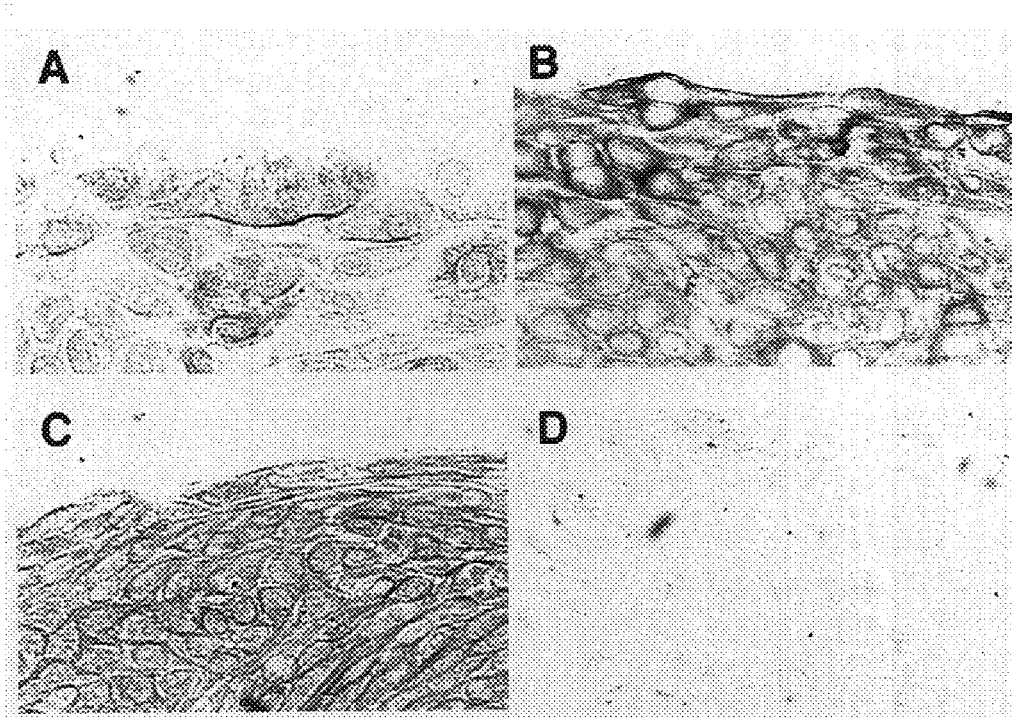
FIG. 2 shows microphotographs of immunoperoxidase staining for several markers on MTE cells.

Monolayer cultures of MTE cells were fixed in situ with 3% paraformaldehyde for about 1 hour. Alternatively, monolayer cultures of MTE cells may be fixed with ethanol at −20 degrees Celsius for about 5 seconds and allowed to air dry. After the fixative was washed away with phosphate buffered saline (PBS), the cells were incubated sequentially in blocking buffer (5% goat serum and 0.1% Tween 20 in PBS) for about 30 minutes then in primary antibodies for about 1 hour, and then with anti-mouse Ig-horse radish peroxidase for about 1 hour with PBS rinses in between the steps. The primary antibodies used were anti-cytokeratin clone 4.62, 8.12, 8.13 and anti-vimentin clone VIM 13.2 from Sigma at the dilution recommended by the supplier. To visualize staining of MTE cells by the antibodies, the MTE cells were incubated in peroxidase substrate $DAB/H_2O_2$ prepared from Sigma tablets. Brown colored product was the indication of the presence of specific antigen (FIG. 2). Staining of cytokeratin in the MTE cells was much stronger than staining of vimentin in the MTE cells.

Example 4

Detection of HOX Gene Transcripts in MTE Cells

Immature Müllerian tract epithelial cells express all three HOX genes, Hoxa9, Hoxa10 and Hoxa11. Taylor H. S. et. al. Biology of Reproduction 57, 1338–1345 (1997). Hoxa9 is restricted to the oviductal cells; Hoxa10 is restricted to endometrial cells; and Hoxa11 is restricted to endocervical epithelial cells. To test the expression of the Hox genes, total RNA was extracted from MTE cells after 5 passages and the RNA was amplified by RT-PCR using Hox-specific primers. The primers used were:

```
Hoxa9:   accagaactggtcggtgat and agaggtacctggagacgat   (SEQ ID NOS: 1-2)

Hoxa10:  cgcagaacatcaaagaagag and tgagaaaggcggaagtagc   (SEQ ID NOS: 3-4)

Hoxa11:  tacgtctcgggtccagat and atggcgtactctctgaaggt    (SEQ ID NOS: 5-6)
```

Figure 3:
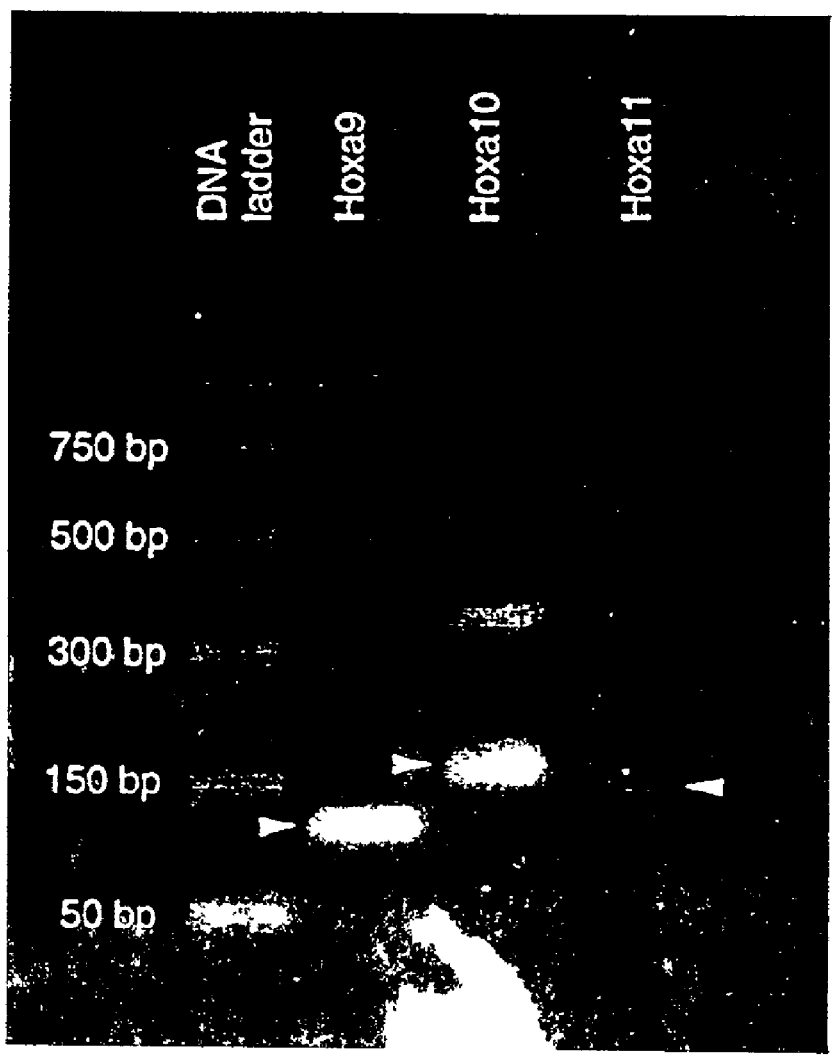
FIG. 3 shows the results of RT-PCR assay wherein PCR primers specific for Hoxa9, Hoxa10, and Hoxa11 genes were used to detect HOX gene transcripts in total RNA extracted from MTE cells. The arrows indicate expected sizes of HOX gene transcript bands.

The PCR products were separated on a 2% agarose gel and the PCR bands were detected by staining the agarose gel with ethidium bromide. All the three HOX genes (Hoxa9, Hoxa10, and Hoxa11) were expressed by MTE cells (shown in FIG. 3). The result was further confirmed by in situ hybridization.

Example 5

Use of MTE Cells for Generating a Human Tissue Model or Cell Therapy

Figure 4:
FIG. 4 show the results of a histological analysis of a Müllerian tract epithelial cell graft recombinant that was transplanted in nude mice. MTE cells formed structures that resembled the endometrium and oviduct. "M" refers to a portion of the mesenchyme, "L" indicates the lumen, the long arrow indicates the location of an apical epithelium, and the short arrow indicates the location of glandular epithelium.

MTE cells harvested from monolayer cultures after 3 passages were combined with rat urogenital sinus mesenchymal tissue to make tissue graft recombinants. The graft recombinant was cultured on agar plates for approximately 24 hours. Thereafter, the graft recombinants were implanted under the kidney capsule in nude (severe combined immunodeficiency or SCID) mice. The implant was allowed to grow for about 2 months before the graft recombinant tissues were excised and analyzed by histology. The result showed the MTE cells formed structure that resembled the endometrium or oviduct (FIG. 4).

What is claimed is:

1. A method of providing a source of an immunogen to a heterologous recipient, comprising: administering to said recipient a substantially pure population of human Müllerian duct-derived epithelial cells in an amount effective to induce an immune response in said recipient; wherein said Müllerian duct-derived epithelial cells have a pluripotent capacity to differentiate into uterine, oviductal, cervical, and vaginal cells.

2. The method of claim 1, further comprising maintaining the Müllerian duct-derived epithelial cells in serum-free media before administering the Müllerian duct-derived epithelial cells to said recipient.

3. The method of claim 1, wherein cell surfaces of said Müllerian duct-derived epithelial cells are substantially free of serum biomolecules.

4. The method of claim 1, further comprising identifying the expression of at least one cell surface marker in said Müllerian duct-derived epithelial cells before administering said Müllerian duct-derived epithelial cells to said recipient, wherein said at least one cell surface marker is selected from the group consisting of cytokeratin 1, cytokeratin 5, cytokeratin 6, cytokeratin 7, cytokeratin 8, cytokeratin 10, cytokeratin 11, cytokeratin 13, cytokeratin 15, cytokeratin 16, cytokeratin 18, cytokeratin 19, and vimentin.

* * * * *